(12) United States Patent
Lundberg et al.

(10) Patent No.: US 11,382,601 B2
(45) Date of Patent: Jul. 12, 2022

(54) METHOD AND APPARATUS FOR ANNOTATING ULTRASOUND EXAMINATIONS

(71) Applicant: FUJIFILM SonoSite, Inc., Bothell, WA (US)

(72) Inventors: Andrew Lundberg, Woodinville, WA (US); Thomas M. Duffy, Snohomish, WA (US); Robert W. Steins, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 803 days.

(21) Appl. No.: 15/909,839

(22) Filed: Mar. 1, 2018

(65) Prior Publication Data
US 2019/0269384 A1  Sep. 5, 2019

(51) Int. Cl.
*A61B 8/08* (2006.01)
*A61B 8/00* (2006.01)
(Continued)

(52) U.S. Cl.
CPC .............. *A61B 8/5207* (2013.01); *A61B 8/08* (2013.01); *A61B 8/0883* (2013.01); *A61B 8/461* (2013.01);
(Continued)

(58) Field of Classification Search
CPC ....... A61B 8/5207; A61B 8/0883; A61B 8/08; A61B 8/5223; A61B 8/585; A61B 8/461;
(Continued)

(56) References Cited

U.S. PATENT DOCUMENTS 6,238,342 B1   5/2001  Feleppa et al.
6,654,728 B1 * 11/2003  Li ......................... G06T 7/0012
                                                   706/2
(Continued)

FOREIGN PATENT DOCUMENTS

CN        105574820       5/2016
JP        2011-115456     6/2011
(Continued)

OTHER PUBLICATIONS

Cheng, P.M. et al., 'Transfer Learning with Convolutional Neural Networks for Classification of Abdominal Ultrasound Images.' J Digit Imaging (2017), 10 pages.
(Continued)

*Primary Examiner* — Sanjay Cattungal
(74) *Attorney, Agent, or Firm* — Womble Bond Dickinson (US) LLP

(57) ABSTRACT

An ultrasound imaging system includes a processor to associate an ultrasound image with one or more pictographs that correspond to the image. A processor provides ultrasound image data to one or more trained neural networks that classify the image data. The processor is programmed to select one or more pictographs that correspond to the classified image data for presentation to the operator. In some embodiments, the processor is programmed to use a neural network to determine if an ultrasound image captured during an examination corresponds to one or more required views for a particular type of examination.

21 Claims, 8 Drawing Sheets

(51) Int. Cl.
*G06N 3/04* (2006.01)
*G06N 3/08* (2006.01)
*G16H 40/63* (2018.01)
*G06F 3/0488* (2022.01)

(52) U.S. Cl.
CPC .............. *A61B 8/463* (2013.01); *A61B 8/465* (2013.01); *A61B 8/5223* (2013.01); *A61B 8/585* (2013.01); *G06N 3/0454* (2013.01); *G06N 3/08* (2013.01); *A61B 8/4427* (2013.01); *G06F 3/0488* (2013.01); *G16H 40/63* (2018.01)

(58) Field of Classification Search
CPC ....... A61B 8/463; A61B 8/465; A61B 8/4427; G06N 3/0454; G06N 3/08; G16H 40/63; G16H 15/00; G16H 50/70; G16H 50/20; G16H 30/40; G06F 3/0488
See application file for complete search history.

(56) References Cited

U.S. PATENT DOCUMENTS

| | | | | |
|---|---|---|---|---|
| 6,970,587 | B1* | 11/2005 | Rogers | G06T 7/0012 128/922 |
| 7,308,126 | B2* | 12/2007 | Rogers | G06K 9/622 382/132 |
| 7,727,151 | B2* | 6/2010 | Zhang | A61B 8/465 600/443 |
| 8,326,012 | B2* | 12/2012 | Kreeger | G06F 3/04815 382/132 |
| 8,483,454 | B2* | 7/2013 | Li | A61B 5/7264 382/128 |
| 8,879,813 | B1* | 11/2014 | Solanki | G06T 5/008 382/128 |
| 8,989,468 | B2* | 3/2015 | Binnig | G06T 7/0012 382/131 |
| 9,146,663 | B2* | 9/2015 | Kreeger | A61B 6/502 |
| 10,706,533 | B2* | 7/2020 | Lynch | G06N 5/022 |
| 2003/0125621 | A1* | 7/2003 | Drukker | G06T 7/0012 600/437 |
| 2003/0212327 | A1* | 11/2003 | Wang | A61B 6/502 600/437 |
| 2004/0068170 | A1* | 4/2004 | Wang | A61B 8/465 600/407 |
| 2005/0111718 | A1* | 5/2005 | MacMahon | G06T 7/0012 382/130 |
| 2005/0171430 | A1* | 8/2005 | Zhang | A61B 8/13 600/437 |
| 2007/0055153 | A1 | 3/2007 | Simopoulos et al. | |
| 2008/0253631 | A1* | 10/2008 | Oosawa | G16H 15/00 382/128 |
| 2009/0082637 | A1* | 3/2009 | Galperin | G16H 50/20 600/300 |
| 2010/0076311 | A1* | 3/2010 | Tabar | A61B 8/0825 600/443 |
| 2011/0257505 | A1* | 10/2011 | Suri | A61B 6/5217 600/408 |
| 2012/0157841 | A1* | 6/2012 | Glaenzer | A61B 8/445 600/439 |
| 2014/0064580 | A1* | 3/2014 | Madabhushi | G06T 7/149 382/128 |
| 2014/0343420 | A1* | 11/2014 | Zhang | A61B 8/0825 600/437 |
| 2016/0287214 | A1 | 10/2016 | Ralovich et al. | |
| 2018/0271502 | A1* | 9/2018 | Zarrine-Afsar | H01J 49/0031 |
| 2019/0000424 | A1* | 1/2019 | Samset | A61B 8/0883 |
| 2019/0122073 | A1* | 4/2019 | Ozdemir | A61B 6/5217 |
| 2019/0237186 | A1* | 8/2019 | El-Baz | G16H 30/40 |

FOREIGN PATENT DOCUMENTS

| | | |
|---|---|---|
| KR | 10-2016-0072677 | 6/2016 |
| WO | 2014162232 A1 | 10/2014 |

OTHER PUBLICATIONS

International Search Report for Application No. PCT/US2019/018438, dated Jun. 11, 2019, 3 pages.
Written Opinion of the International Searching Authority for Application No. PCT/US2019/018438, dated Jun. 11, 2019, 5 pages.
International Preliminary Search Report and Written Opinion on the Patentability of Application No. PCT/US2019018438, dated Sep. 10, 2020, 6 pages.
Extended European Search Report on the Patentability of Application No. 19760021.6 dated Oct. 18, 2021, 8 pages.
Cheng Phillip M et al: "Transfer Learning with Convolutional Neural Networks for Classification of Abdominal Ultrasound Images", Journal of Digital Imaging, Springer-Verlag, CHAM, vol. 30, No. 2. (2016-11-228), pp. 234-243.

* cited by examiner

METHOD AND APPARATUS FOR ANNOTATING ULTRASOUND EXAMINATIONS

TECHNICAL FIELD

The disclosed technology relates generally to ultrasound imaging systems and in particular to systems for associating pictographs with ultrasound images.

BACKGROUND

As will be appreciated by those skilled in the art, most modern ultrasound imaging systems work by creating acoustic signals from a transducer having a number of individual transducer elements that are formed in a sheet of piezoelectric material. By applying a voltage pulse across an element, the element is physically deformed thereby causing a corresponding ultrasound signal to be generated. The signal travels into a region of interest where a portion of the signal is reflected back to the transducer as an echo signal. When an echo signal impinges upon a transducer element, the element is vibrated causing a corresponding voltage to be created that is detected as an electronic signal. Electronic signals from multiple transducer elements are combined and analyzed to determine characteristics of the combined signal such as its amplitude, frequency, phase shift, power and the like. The characteristics are quantified and converted into pixel data that is used to create an image of the region of interest.

When a sonographer performs an ultrasound examination of a patient, it is common to select one or more of the images to be stored in a medical record. Typically the images selected by the sonographer are taken from one of several common viewing angles. For example, when imaging the heart, there are several well-known or standardized positions on the body where a clear view of the heart muscle can be obtained through or under the rib cage. To help identify the view of the patient's anatomy that is shown in an image, a sonographer will often associate or place a pictograph (sometimes referred to as a pictogram) on the image. A pictograph is a simplified ultrasound image or other symbol representing a tissue type or an image feature seen from a particular location and/or viewing angle. In some embodiments, a pictograph can also be or include a text annotation such as "Liver", "Heart", "Mitral Valve" or the like. The pictograph is immediately recognizable to a sonographer or physician and is used to help interpret the actual ultrasound image that was obtained from the patient.

In current ultrasound imaging systems, pictographs associated with many possible tissue types or image features and viewing angles are stored in the imaging system's memory. If a sonographer wants to add a pictograph to an image, the sonographer must select a particular pictograph from all available pictographs. Some systems group pictographs by tissue types. For example, a subset of pictographs for liver tissue may be stored in one folder while another subset of pictographs for cardiac tissue are stored in another folder etc. Even with the pictographs sorted by tissue types, the operator still has to navigate to the correct folder and select the pictograph that best matches the orientation of the probe used to obtain the image being saved. The result is a somewhat cumbersome process whereby the sonographer has to view multiple pictographs in order to select one or more that have the closest match to the ultrasound image being saved.

SUMMARY

To address these and other concerns, the technology disclosed is directed to an ultrasound imaging system that automatically presents one or more pictographs corresponding to an ultrasound image that is obtained by a sonographer. The sonographer can select a pictograph from the one or more presented pictographs to be stored in association with the ultrasound image.

In one embodiment, the ultrasound imaging system employs artificial intelligence such as a trained convolutional neural network to classify an image based on features that are either present or not present in the image. A processor then presents one or more pictographs corresponding to the classified image. A processor presents a subset of pictographs that correspond to the classified image and can be selected by the sonographer to annotate the ultrasound image.

In another embodiment, an ultrasound examination type is associated with one or more desired ultrasound image views that are required for the type of examination. A neural network, such as trained convolutional neural network, compares ultrasound data for multiple ultrasound images obtained by the sonographer and identifies one or more images that correspond to the required ultrasound views. The operator can accept one or more of the identified images for storage in a patient record for a particular examination.

DETAILED DESCRIPTION

Figure 1:
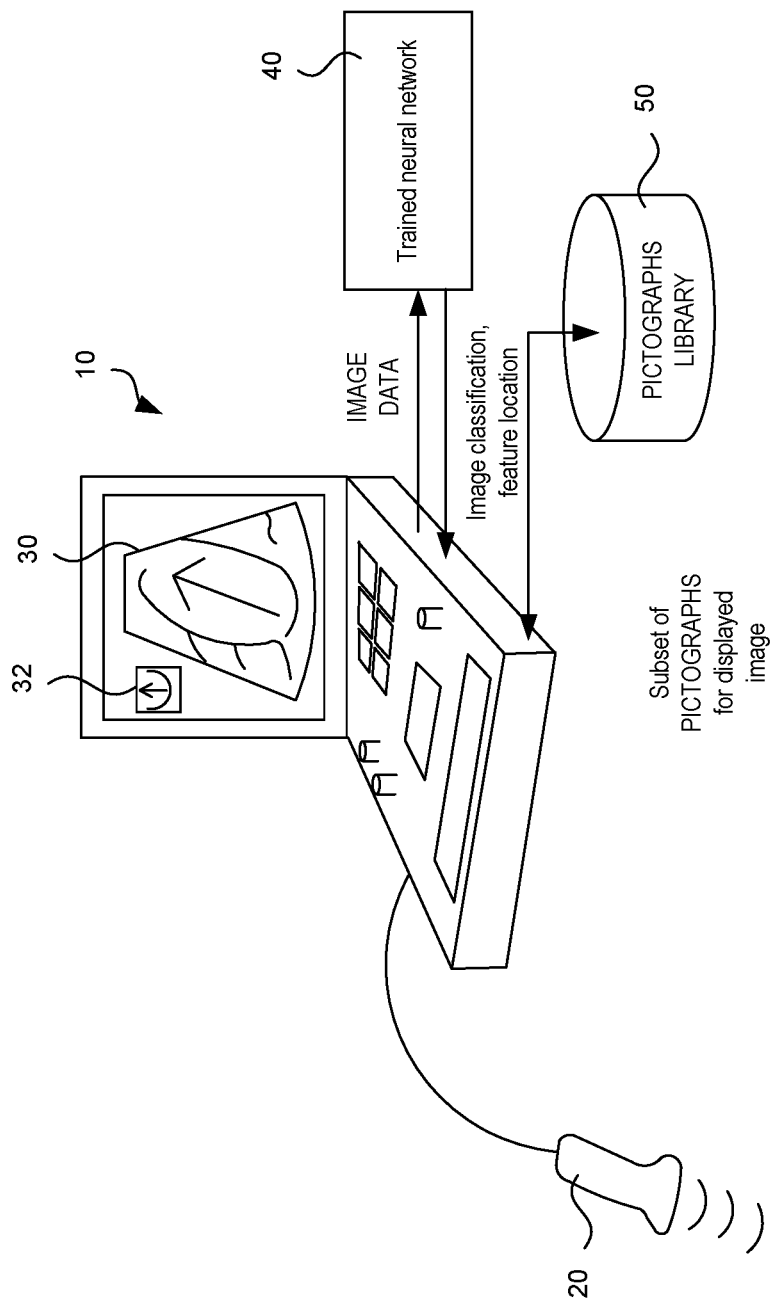
FIG. 1 illustrates a representative ultrasound imaging system in accordance with an embodiment of the disclosed technology.

FIG. 1 shows a representative ultrasound imaging system 10 in accordance with one embodiment of the disclosed technology. The ultrasound imaging system may be a portable, handheld or cart-based system of the type that includes one or more imaging transducers 20. The imaging transducer 20 generates acoustic ultrasound signals and detects the corresponding ultrasound echoes. Image processing circuitry in the ultrasound imaging system receives electronic signals corresponding to the ultrasound echoes and processes the signals to produce a series of images 30 of the area being examined. The ultrasound imaging system 10 generally has one or more video displays on which the ultrasound images are displayed. One or more of the displays may be touch sensitive so that an operator can operate the imaging system with a graphical user interface on the display or by using more conventional input devices on the imaging system itself such as a keyboard, trackball, touch pad, buttons, voice commands etc. In some embodiments, the ultrasound imaging system may be connected to an auxiliary display or computing device (not shown) such a remote server, tablet, laptop, smart phone etc. via a wired or wireless communication link. The auxiliary computing device can be used as another video screen, input device and/or to provide additional computing power for the imaging system.

As indicated above, there are instances where a sonographer wants to annotate an ultrasound image with a pictograph 32 that represents a tissue type or image feature under examination and may be specific to the view (orientation of the imaging probe) with which the ultrasound image 30 is obtained. Because the pictographs are simplified images, graphic symbols or text annotations, the pictograph 32 serves to aid a radiologist, physician or sonographer in understanding what the actual ultrasound image 30 is trying to show. To simplify the task of selecting a corresponding pictograph for a particular ultrasound image, a processor (e.g. CPU, GPU, DSP, FPGA, ASIC, dedicated integrated circuit or a combination of processors or the like) in the ultrasound imaging system 10 employs artificial intelligence to classify the ultrasound image 30. In one embodiment, once the operator has captured an image that they would like to associate with a particular pictograph, the operator enters a command, such as by touching a GUI on a screen, pressing a button, saying a speech command etc., which causes the processor identify one or more pictographs that correspond to the image. The processor is configured to execute a series of instructions that are stored in a processor-readable memory or to operate according to pre-configured logic to implement a trained neural network such as a convolutional neural network 40. The neural network 40 is trained to classify an input ultrasound image (or portion of the image) based on image features that are present (or not present) in the image. For example, images can be classified as one of several different tissue types or image features (heart tissue, liver tissue, breast tissue, abdominal tissue, bladder tissue, kidney tissue, heart valves, vessels etc.). In one embodiment, the neural network 40 returns a list of calculated values representing how likely the image corresponds to a number of particular classifications (tissue type, image feature, lack of a particular feature in an image or other criteria that the neural network is trained to recognize). Such calculated values may be a probability that an image is a particular tissue type (e.g. cardiac tissue=0.72) or may be a probability that the image contains a particular anatomical feature (carotid artery=0.87) or lacks an image feature (no kidney tissue=0.87) etc. Upon receipt of the determined probabilities from the neural network, the processor is programmed to recall one or more pictographs that are stored in a pictograph library 50 or other memory of the ultrasound imaging system and that correspond to the classified image. In some embodiments, the trained neural network is resident on the ultrasound imaging system itself. However, if the ultrasound imaging system is connected to a computer communication link, then the trained neural network can be located on a remote computer system and supplied with images to be analyzed that are provided by a processor of the imaging system.

The pictograph library 50 may be arranged as a database with links to various pictographs that are categorized by image features or may be series of folders that contain the pictographs grouped by image features. Other ways of organizing the pictographs in memory such as by tagging them with meta data specifying various image features are also possible. In some embodiments, the processor may be programmed to make a request for the corresponding pictographs from a remotely located computing device. For example, the processor in the ultrasound imaging system can request the transmission of all pictographs stored on a remote computing device that correspond to cardiac tissue or to liver tissue or for those that lack a carotid artery etc.

In some embodiments, the processor displays the one or more of the pictographs corresponding to the classified image on a video display screen of the ultrasound imaging system or auxiliary system and the operator can select which pictographs(s) they would like to use to associate with or to annotate the ultrasound image 30. For example, if the neural network returns a probability value such as "cardiac tissue=0.98," the processor executes program steps to retrieve one or more of the pictographs associated with cardiac tissue from a folder in the pictograph library, from a pictograph database or from a remote computing device. In some embodiments, the use of more than one neural network allows more specific pictographs to be retrieved. For example, if a first neural network is trained to identify the type of tissue and returns a value such as "cardiac tissue=0.98," then the classified image can be provided to a second cardiac-specific neural network that is configured to return probability values of how likely the image is from a particular view. If the second neural network returns a value such as "apical view=0.92," then one or more of the pictographs corresponding to apical views of the heart can be retrieved and presented on the video display screen for the operator to select in response to a command to retrieve the corresponding pictograph(s). In other embodiments, a single neural network is trained to classify images by both tissue type and a view shown in an image.

Some ultrasound imaging systems allow the operator to program the system for a particular examination type or to adjust imaging parameters for particular types of tissue. For example, the operator may select imaging parameters for an abdominal examination or that are optimized for imaging heart tissue etc. In some embodiments, the ultrasound imaging system can keep a record of the type of examination being performed and can compare the type of examination set or the values of the imaging parameters that are set by the operator with the classification of the image as determined by the trained neural network(s). In one embodiment, once the operator has obtained an image of the tissue that they would like to associate with a pictograph, the operator enters a command to cause the processor to supply the image to the neural network(s). If the image classified by the neural network corresponds to the imaging parameters used for that type of examination, then the processor can assign a higher probability to the type of tissue identified by the neural network 40. If the type of examination set on the imaging system or the imaging parameters do not agree with the classification of the image by the neural network, the processor may ask the operator to check the settings on the ultrasound imaging system and may suggest that the operator change the settings to those that are optimal for the type of tissue identified by the neural network. For example, upon capturing an ultrasound image of the liver, the operator initiates a command to identify an associated pictograph for the image. The neural network classifies the image as having a high probability that the type of tissue in the image is heart tissue. The processor compares this result to the record of how the imaging system is programmed and determines that the type of anatomy imaged (e.g. heart tissue) does not correspond to the type of examination being performed (e.g. liver examination). The processor is therefore programmed to prompt the operator to change the imaging parameters (or have the imaging system select the imaging parameters) to better suit the type of tissue detected or in some embodiments to confirm that the operator wants to continue with the imaging parameters they have set. In some embodiments, the classification of the images by the processor can be performed without the user having to request that a pictograph be associated with the image. For example, the first few images generated during an examination may be classified to confirm that the examination type or imaging parameters are optimized for the type of tissue detected.

Figure 2:
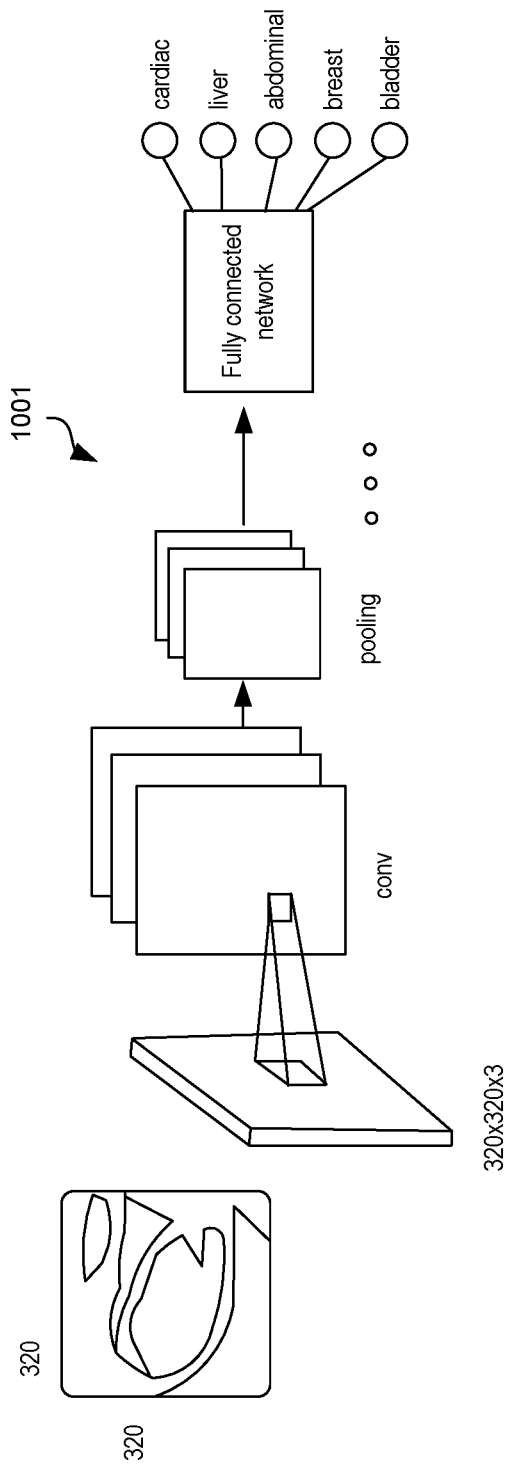
FIG. 2 illustrates a representative convolutional neural network used to classify features of an input ultrasound image in accordance with one embodiment of the disclosed technology.

FIG. 2 illustrates one possible embodiment of a trained neural network 100 that is configured to classify an input ultrasound image 120. As will be appreciated by those skilled in the art, there are numerous types of neural networks that can be used to identify features that are present or not present in a digital image. One of the more common networks for image analysis is a convolutional neural network. In one embodiment, a trained convolutional neural network takes an input image of a predetermined size (e.g. a matrix of 320×320 pixel values or another size, which may or may not be square) and convolves a number of filters (e.g. a matrix of filter values) over the image. In the case of a color ultrasound image, each pixel generally stores pixel intensity values for red, green and blue color components. Filters are convolved with the pixel intensity numbers for each color component. The filters are designed to react to features in the image. Multiple convolutional steps can be used. In most convolutional networks, pooling is performed that reduces the size of the output matrices by analyzing groups of matrix values (e.g. 5×5 etc.) and taking their maximum, average or the like to define a single entry in an output matrix. Further convolutions can be performed on the pooled values. Depending on the type of neural network used, the filtered and pooled values are further processed such as by providing the values to a fully connected layer that indicates how likely the image has a particular classification. For example, the fully connected layer can provide an output comprising a percentage likelihood that an input image corresponds to different tissue types. In the example shown in FIG. 2, the trained neural network produces estimations (probabilities) of how likely an input image represents various tissue types such as cardiac, liver, abdominal, breast or bladder anatomical features. In one embodiment, the processor is programmed to receive the probability values and retrieve one or more pictographs representing the most likely determined tissue type. If further classification is required, then the processor provides the classified image to one or more other neural networks to further classify the image. For example, cardiac tissue images can be classified in a neural network that is trained to identify the views with which such images are obtained such as parasternal, apical, subcostal or suprasternal notch views. The processor receives the likelihood that an image represents each of these different views and can retrieve the pictograph representing the most likely determined tissue type and view.

Figure 3:
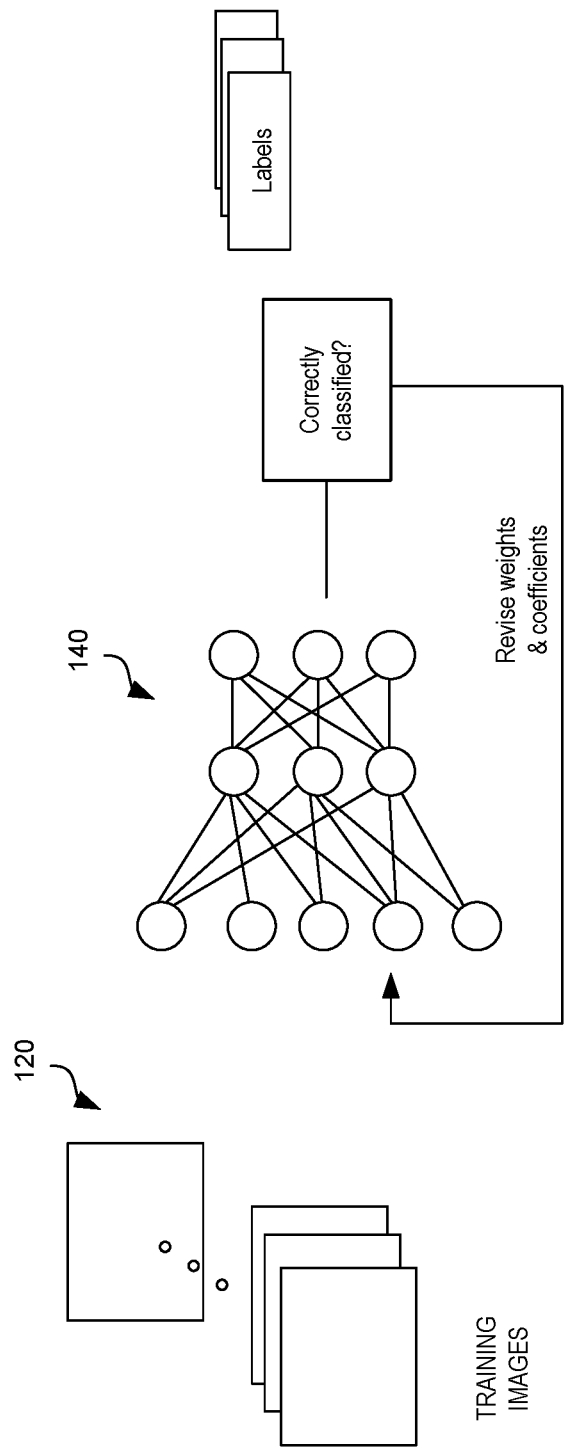
FIG. 3 illustrates a process of training a neural network to be used in an ultrasound imaging system in accordance with one embodiment of the disclosed technology.

FIG. 3 illustrates one representative system for training a neural network to classify a number of ultrasound images. In one embodiment, a training set of many (e.g. thousands+) of ultrasound images 120 that have been classified by image features are supplied to a neural network 140 that is typically created with an available software package. The neural network 140 is trained with the images 120 to classify the presence or absence of features in an image. In some embodiments, filter and bias values for the nodes of the neural network are initially given random values and the training system then uses mathematical searching techniques to identify changes to the parameter values that reduce the error rate of misclassified images. The result of the training process is a set of network parameter values that allow the neural network 140 to correctly identify or classify the training images to within a desired level of accuracy. The greater the number of training images in the training set, the more accurate the network parameters values may be. Once the neural network is trained, the values of the various parameters are used by the neural network 140 to classify actual images such as images obtained by the ultrasound imaging system. In other embodiments, the trained neural network is implemented by a processor that is different than the processor of the ultrasound imaging system. The details of how neural networks operate and how they are trained based on a set of classified input training images are well known to those of ordinary skill in the art of artificial intelligence.

Figure 4:
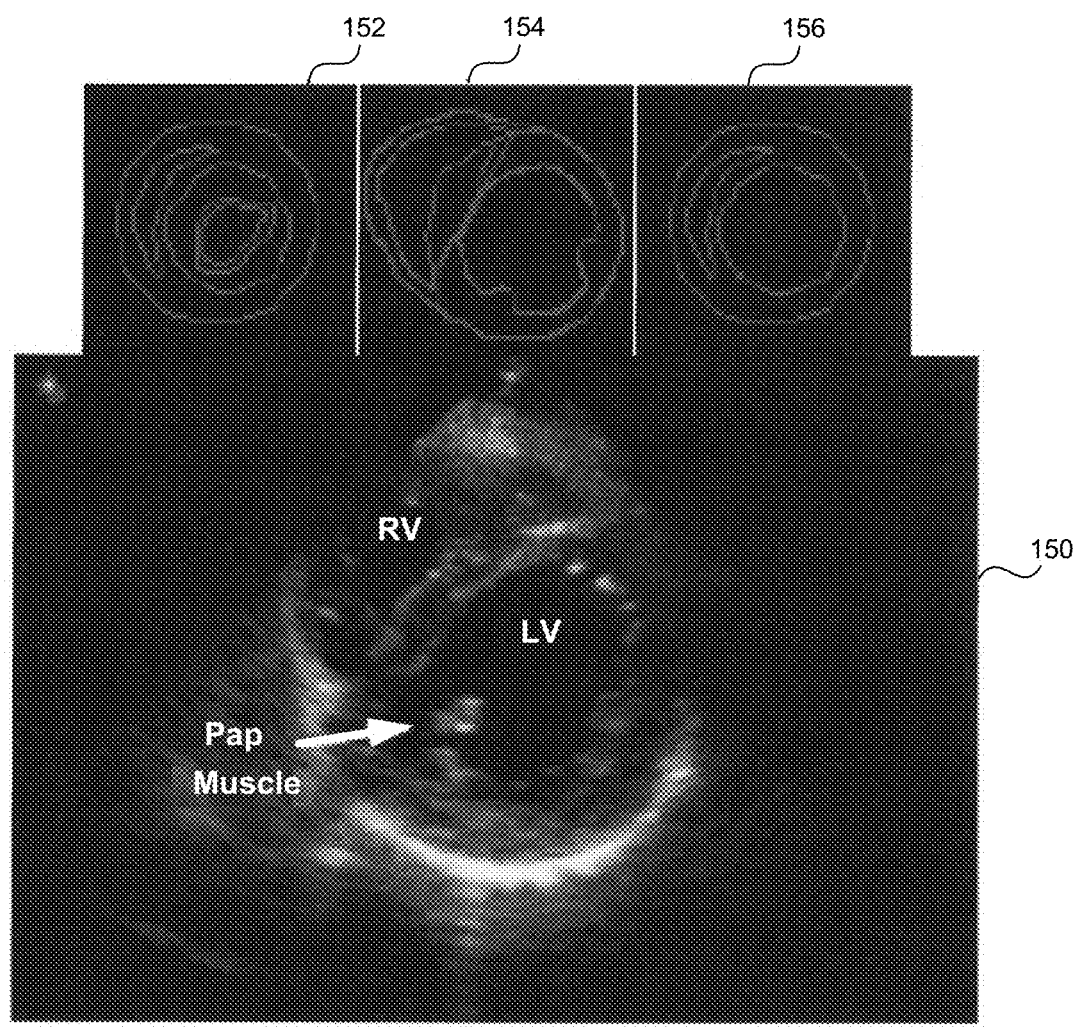
FIG. 4 illustrates a representative ultrasound image with a number of presented pictographs that can be selected by an operator to annotate the ultrasound image in accordance with an embodiment of the disclosed technology.

FIG. 4 illustrates an ultrasound image 150 that is obtained by a sonographer and a number of pictographs 152, 154, 156 that are selected and presented on a video display by the ultrasound imaging system as a result of providing data for the ultrasound image 150 to the trained neural network. In this example, the neural network(s) determine that the image 150 most likely represents cardiac tissue using the subcostal window showing a cross section of the left and right ventricles. The processor in the imaging system receives the image classification from the neural networks and then retrieves from memory one or more pictographs that correspond to the most likely determined tissue and view type and displays them on a video display and/or auxiliary system.

With the pictographs 152, 154, 156 displayed, the operator is able to select one or more pictographs for association with the ultrasound image. In the example shown, the pictographs 152, 154 and 156 are all associated with cardiac tissue and subcostal views. In one embodiment, the operator is then free to select one or more of the presented pictographs to be associated with the ultrasound image 150 for inclusion into a patient medical record. In some embodiments, the pictographs are presented by displaying them on a video monitor in an order that is indicative of how likely each pictograph corresponds to the classified image from most likely to least likely or vice versa. In another embodiment, the pictographs are color coded in a manner that indicates how likely each pictograph corresponds to the classified image (green=most likely, red=least likely etc.) In yet another embodiment, the pictographs are shown with a visual cue (number, score, word description such as most likely, least likely etc.) that indicates how likely each pictograph corresponds to the classified image. Presentations of pictographs may involve showing all those pictographs corresponding to an identified tissue type. For example, if the neural network classifies an image as showing heart tissue, then only pictographs corresponding to heart tissue are presented. In another embodiment, pictographs are presented by not showing pictographs that do not correspond to the classified image. For example, if an image is classified as showing heart tissue then pictographs corresponding to kidney tissue are not presented. In some embodiments, only a subset of the pictographs that possibly correspond to the ultrasound image are presented at once. Such pictographs can be shown with their confidence value or by a color code etc. so that the operator is able to easily identify the most likely pictographs. If the operator doesn't like any of the pictographs presented, they can view other pictographs that are slightly less likely candidates. In some embodiments, the possible set of pictographs need not be stored on the ultrasound imaging system itself. The pictographs presented to the operator can be retrieved from a local memory or a memory of a remote source over a wired or wireless communication link in response to a request specifying the classification(s) of the image identified by the neural networks.

With the one or more pictographs presented based on the image classification determined by the trained neural network, the processor is programmed to determine which pictograph, if any, is selected. Once the operator has selected the desired pictograph using commands supplied to the GUI, voice commands, button presses or the like, the ultrasound image can be stored with the selected pictograph. In some embodiments, the pixels of the pictograph are blended with the pixels of the ultrasound image and in other embodiments, the ultrasound image is stored with metadata that indicates which pictograph is to be displayed with the image and where the pictograph is to appear as an overlay on the image.

In some embodiments, a neural network is trained to identify where to place the pictograph in an image. For example, if a pictograph represents a kidney, a trained neural network is configured to identify a prominent feature of the kidney in an image. An image classified as including kidney tissue is given to the trained neural network that returns the probability of each portion of the image containing the prominent feature. The portion or area of the image with the highest probability is used by the processor as a location to place the pictograph adjacent the prominent feature. Alternatively, labels associated with the pictograph can be placed adjacent identified features in an image. In some embodiments, the neural network can be trained to detect free space in an image and used as the location to place the pictograph or the annotation. If the user does not like the location selected for the pictograph or labels, the user is free to move them to a new location in the image.

In this embodiment, the trained neural network and processor operate to limit the number of possible pictographs that need to be viewed by the operator in order to find a corresponding pictograph for any particular ultrasound image. As will be appreciated, by reducing the number of pictographs that an operator has to view in order to select a pictograph that is associated with the image created by the ultrasound imaging system, workflow speed is increased and the examination process is simplified.

In the embodiment described above, the pixel values supplied to the neural network are color brightness values. It will be appreciated that black and white pixels could also be used by supplying for example, only brightness intensity values as inputs to a neural network that is trained to classify black and white ultrasound images. In some embodiment, pre-pixel data for an image such as, but not limited to, pre-scan conversion data, beamformed echo data or RF data for an image can be provided to the neural network to classify the image.

Figure 5:
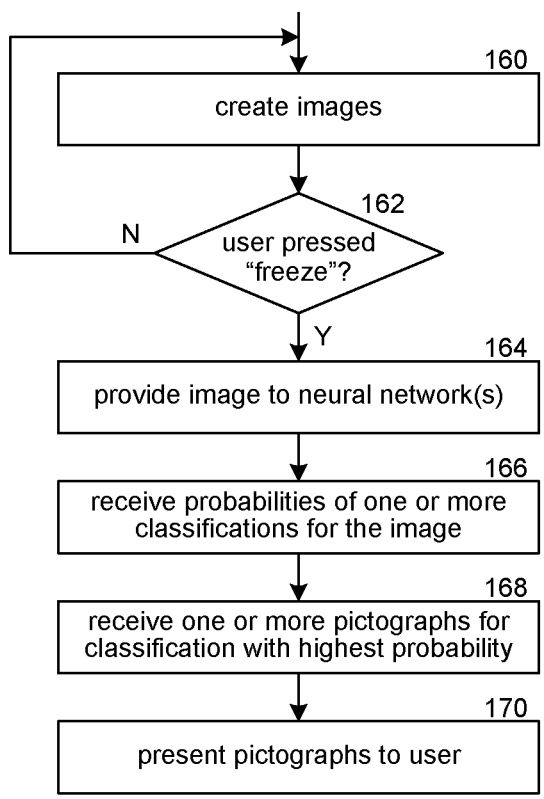
FIG. 5 is a flow chart of steps performed by a processor to associate one or more pictographs with an ultrasound image in accordance with one embodiment of the disclosed technology.

FIG. 5 is a flow chart of steps performed by a processor to determine one or more pictographs that can be associated with an ultrasound image in accordance with one embodiment of the disclosed technology. Although the steps are described in a particular order for ease of explanation, it will be appreciated that the steps could be performed in a different order or that alternative steps could be performed in order to achieve the functionality described.

Beginning at 160, the processor of the ultrasound imaging system is operated in an imaging mode to create ultrasound images in response to ultrasound signals transmitted into a patient and from the ultrasound echo signals that are received from the patient. At 162, the processor detects if the operator has activated a "freeze" button or a similar feature that causes the ultrasound imaging system to capture an ultrasound image. Once the operator has captured the image data, the ultrasound imaging system begins executing steps to determine one or more pictographs that correspond to the image.

At 164, the processor provides the captured image data to one or more trained neural networks such as convolutional neural networks to classify the image as having or not having one or more image features. At 166, the processor receives the output of the neural network(s). Depending on how the networks are designed, such an output can comprise the probability of the input image corresponding to one or more tissue types. In some embodiments, the neural networks return a number of values (e.g. 0.05, 0.05, 0.05, 0.8, 0.05 etc.) that represent the probabilities that the image is of a certain tissue type.

At 168, the processor then receives one or more of the pictographs associated with the classified image. For example, if the neural network identified a particular image as having a high probability of being cardiac tissue, the processor can recall pictographs representing cardiac tissue from memory. Such pictographs can be identified by name or by an ID number that is used to retrieve the pixel values (or text) for the pictograph from a local memory, from a remote location or an auxiliary device (laptop, remote server, smart phone etc.). For example, the processor can send the ID number of the identified pictograph or an indication of the classified image type to a remote location or auxiliary device and receive the corresponding pictograph.

At 170, the processor presents the pictographs corresponding to the classification of the input image to the operator. The operator can then select which, if any, of the pictographs are to be blended into, or stored in association with, the ultrasound image in a patient record. In some embodiments, step 170 can be skipped by the processor and the pictograph that most closely corresponds to the classified input image can be blended into or stored with the input image without requiring the operator to approve the pictograph. The result is that in some embodiments of the disclosed technology, the ultrasound imaging system is able to quickly identify pictographs corresponding to an input image without the operator have to select particular pictographs from all possible pictographs that are associated with an examination type, thereby speeding workflow and providing an easier examination process.

In the embodiment described above, images are sent to the neural network when the user hits a "freeze" button or similar feature. In other embodiments, images are sent to the neural network without requiring user input such as continuously or when the user has completed an examination to identify a corresponding pictograph for the image created.

In another embodiment of the disclosed technology, the sonographer may operate the ultrasound imaging system to create a number of ultrasound images. The sonographer therefore has to choose which image(s) should be saved into a patient record. For example, a patient worksheet or other rule set for a particular examination type may require images of the heart be obtained from three different views.

In this embodiment, a neural network is trained to determine the likelihood that an ultrasound image represents a particular view. In one embodiment, a rule set for a particular examination type defines which views are to be included in a patient report. The trained neural network analyses one or more of the ultrasound images obtained by the sonographer to determine how likely any particular image represents a desired view. The images that have the highest probability of representing the desired view can be presented to the operator for inclusion into the patient record. For example, if image-1 has a 0.87 probability of representing a required view and image-2 has a 0.91 probability of representing the required view, then image-2 is presented to the operator for possible incorporation into the patient record. The image(s) that bears the closest resemblance to a required view is therefore automatically selected by the processor for possible inclusion into the patient report. In some embodiments, a pictograph associated with the selected image is also blended into or associated with the image selected for inclusion into the patient record.

Figure 6:
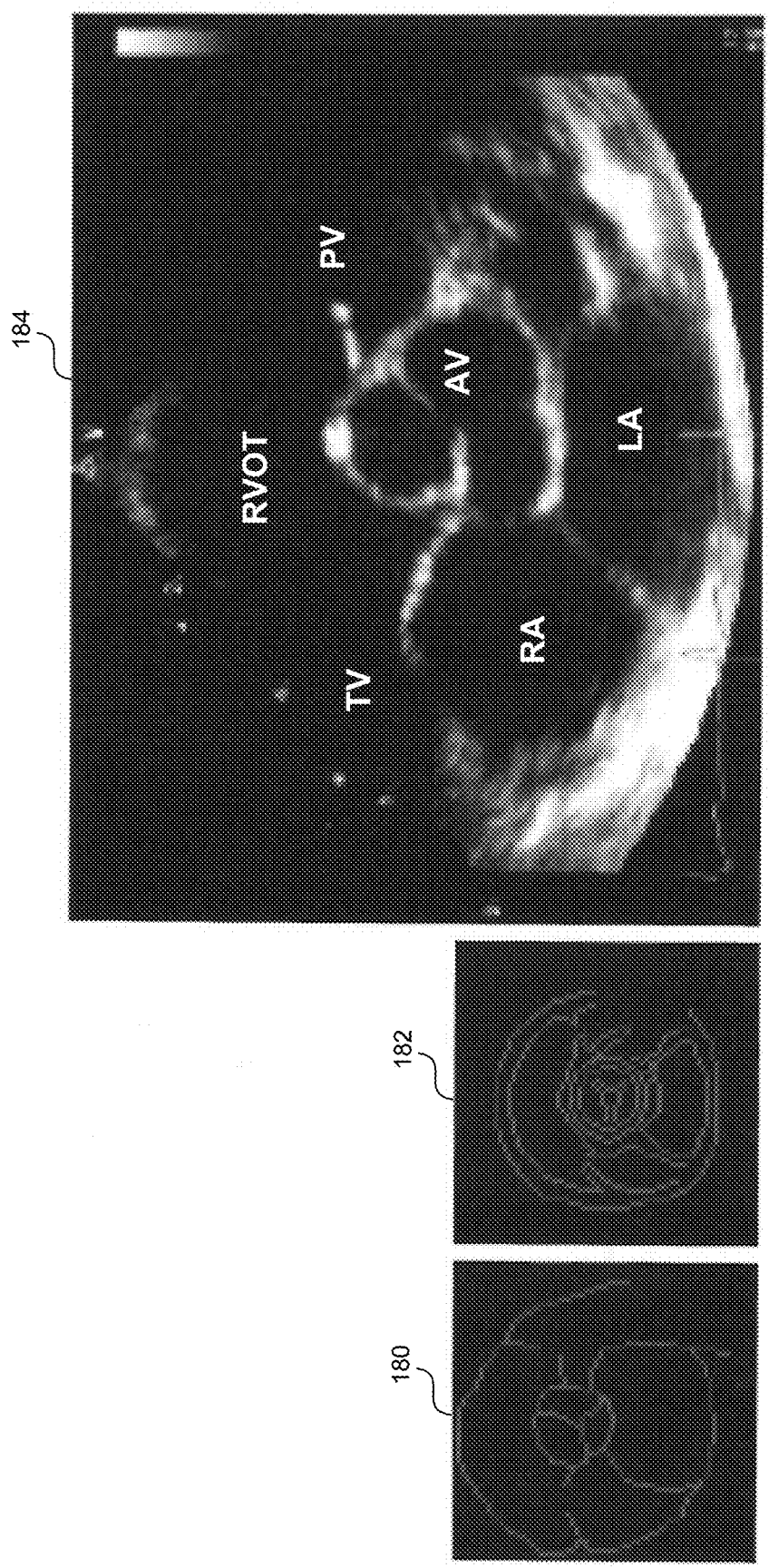
FIG. 6 illustrates a pair of pictographs representing views required for a cardiac examination and a corresponding ultrasound image selected by a neural network that correspond to a required view in accordance with another embodiment of the disclosed technology.

FIG. 6 shows two pictographs 180, 182 representing required cardiac ultrasound images taken with different views for a particular examination type. The rules for the examination type require that the sonographer include an image corresponding to these pictographs in the patient record. Rather than having to manually evaluate all the images that are captured by the ultrasound imaging system, the ultrasound imaging system provides a number of ultrasound images to one or more trained neural networks. The trained neural networks operate to classify the image to determine if one or more correspond to a desired view. Once one or more images 184 are identified that correspond to a desired view, the identified images can be shown to the operator to select which image(s) are to be included in the patient report. In some embodiments, the processor presents the identified images in an order that are ranked by how likely the image corresponds to a desired view and the user can select which image to include in the patient report.

In some embodiments, the ultrasound image that is determined by the neural network as having the highest probability of corresponding to a required view is incorporated into a patient record by the processor without having the operator select the image from a presentation of two or more possible ultrasound images.

In some embodiments, there may be a number of differently trained neural networks, each trained classify different features of an image. For example, a first neural network can be configured to identify the type of tissue in an image and another set of tissue-specific neural networks are trained to identify the views of different tissue types. The processor is therefore programmed to provide the image to a series of neural networks to classify the image and determine if it represents a required view.

In some embodiments, the rules for a particular examination may be defined by pictographs that represent the desired views. In some embodiments, the pictographs are associated with meta data representing for example, the tissue type and view shown by the pictograph. The processor is programmed to analyze the meta data in order to determine the required tissue and view type and to provide ultrasound image data to the corresponding neural networks to determine if the image represents a desired view.

Figure 7:
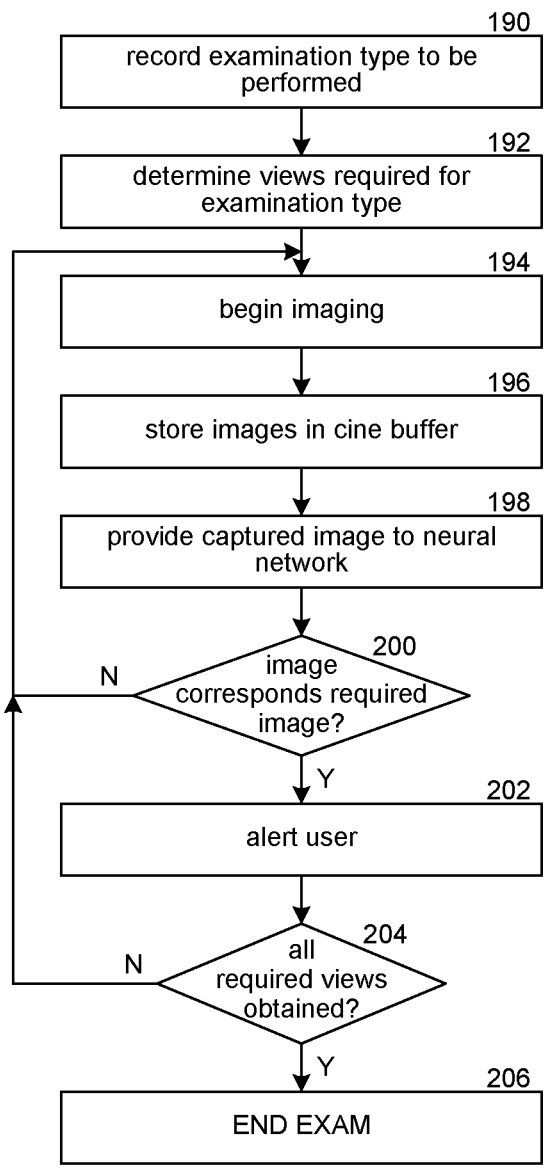
FIG. 7 is a flow chart of steps performed by a processor to identify one or more ultrasound images that correspond to required views for an examination type in accordance with another embodiment of the disclosed technology.

FIG. 7 shows a series of steps performed by a processor of an ultrasound imaging system in accordance with one embodiment of the disclosed technology to identify ultrasound images representing a desired view. Although the steps are described in a particular order for ease of explanation, it will be appreciated that the steps could be performed in a different order or that alternative steps could be performed in order to achieve the functionality described. Beginning at 190, the processor determines and records the type of examination being performed by the operator. At 192, the processor determines one or more ultrasound views that are required for the type of examination being performed. The required views may be programmed in the software of the ultrasound imaging system. Alternatively, the required views could be specified by a patient worksheet to be filled in by the operator. In other embodiments, the required views are specified by a remote computer or auxiliary computer or smartphone in response to a submission from the ultrasound imaging system of what type of examination is being performed. For example, if a patient has a certain insurance plan that requires particular views, the ultrasound imaging system can send a message with "patient ID, exam type" to the insurance company and receive an indication of what views are required for reimbursement. The required views may be coded or specified by pictographs with meta data indicating the required tissue type and views.

At 194, the operator begins the imaging process and at 196, images produced by the imaging system are stored in a cine buffer or other memory. At 198, ultrasound image data for the stored images are provided to one or more trained neural networks to classify the images.

At 200, the processor determines if the image data corresponds to a required view. If so, the ultrasound system preferably alerts the operator that a desired view has been obtained. Examples of such an alert can include an audible or visual queue that a corresponding image has been obtained. If the desired views are represented by pictographs, the alert can place a check by the pictograph corresponding to the desired view or show the pictograph in a different color. Other alerts or indications can include printed messages or audible cues provided to the user on a display screen or from a speaker etc. At 204, the processor determines if all required views are obtained, the system provides an alert or indication to the user that all required images are obtained. If not, the user can be alerted to the fact that one or more required views are not yet obtained and processing returns to 194 and more images are obtained. If all required views are obtained, then the examination can stop at 206.

In some embodiments, a user presses an "end of exam" control or other key specifying the end of the examination before images are analyzed with the neural networks to identify those that correspond to the required views. Alternatively, the processor may detect that the operator has not interacted with the machine for more than a threshold time such as by moving the transducer or interacting with an operator control to infer that the examination has ended.

As indicated above, in some embodiments, the processor executes program steps to automatically select ultrasound images for incorporation into a patient record without requiring the operator to confirm the selection.

In some embodiments, the entire ultrasound image is provided to the neural network(s). In other embodiments, a portion of the image is provided to the neural network. For example, a smaller subset of the pixels defining an image can be sent to the neural network. A sliding window can select which pixel values are sent to the neural network. In this way, the processor is able to determine which portion of an image most closely corresponds to a required image. As will be appreciated, applying multiple sliding windows of pixel values increases the processing time compared with providing an entire ultrasound image to the trained neural network.

Figure 8:
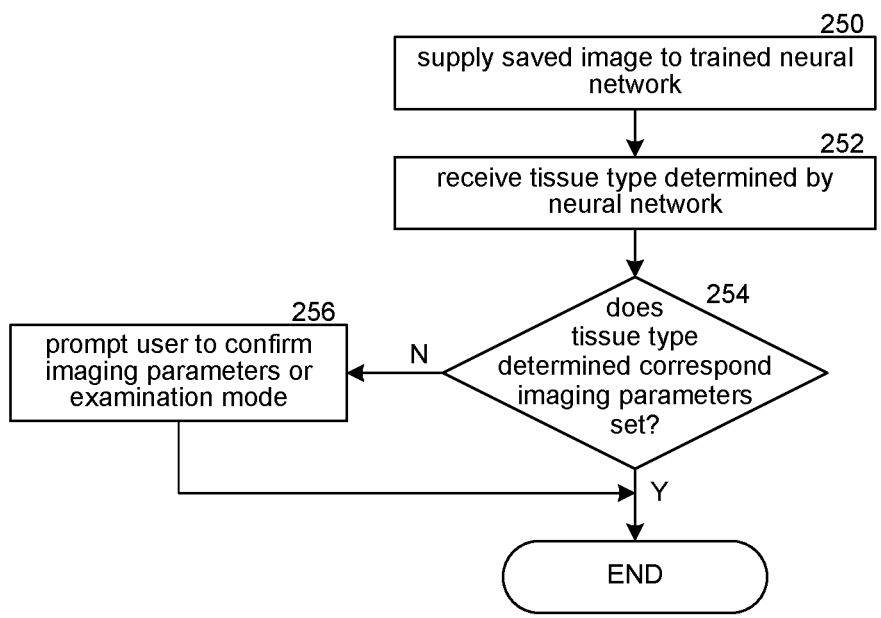
FIG. 8 is a flowchart of steps performed by processor to confirm that imaging parameters are appropriate for a type of anatomy being imaged in accordance with another embodiment of the disclosed technology.

As indicated above, in some embodiments, the disclosed technology is used to confirm that the operator of the ultrasound system is using the correct settings for the type of examination being performed. FIG. 8 shows a sequence of steps performed by a processor to confirm that the image settings are appropriate or correct for the actual images being captured. As used herein "appropriate" or "correct" means that the images produced could not be significantly improved by changing the imaging parameters. An appropriate or correct imaging parameter need not be optimum but would be close enough so that a skilled sonographer would not immediately understand the parameters to be far from optimum. Although the steps are described in a particular order for ease of explanation, it will be appreciated that the steps could be performed in a different order or that alternative steps could be performed in order to achieve the functionality described.

Beginning at 250, the processor in the ultrasound system supplies a saved image to a trained neural network to identify the type of tissue that is shown in the image. At 252, the processor receives the type of tissue identified back from the trained neural network. At 254, the processor determines if the type of tissue identified by the trained neural network corresponds to pre-set imaging parameters (such as but not limited to: gain, frame rate, line density, acoustic power, sector size, available worksheets etc) set on the ultrasound imaging system or the type of examination selected. For example, if the operator has selected imaging parameters that are optimized for liver imaging and the tissue identified by the neural network is heart tissue, then the ultrasound system can prompt the user to either confirm that the correct set of ultrasound imaging parameters are selected or that the correct type of examination set at 256. If the imaging parameters or the type of examination on the ultrasound imaging system correspond to the detected tissue type, then the process ends at 258 with no recommendation to confirm/modify the imaging parameters or the examination type. The neural network in this embodiment therefore acts to reduce the likelihood that incorrect sets of imaging parameters are being used to perform an examination.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a processor on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program for execution by a processor (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code).

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

As will be appreciated, the disclosed technology is not limited to the particular embodiments described above and that changes could be made without departing from the scope of the invention. For example, although the disclosed embodiments are described with respect to human subjects, it will be appreciated that the disclosed technology can be used in veterinary environments as well. Accordingly, the invention is not limited except as by the appended claims.

We claim:

1. An ultrasound imaging system, comprising:
   a memory; and
   a processor coupled to the memory that is configured to:
      provide ultrasound data for an ultrasound image to a neural network;
      receive, from the neural network, a first value indicating a probability that the ultrasound image is of a first feature;
      receive, from the neural network, a second value indicating the probability that the ultrasound image is of a first view based on the first value;
      identify one or more pictographs representing the first view based on the second value, wherein the first view corresponds to a viewing position of an imaging probe used to obtain the ultrasound image; and
      display the one or more pictographs with the ultrasound image on a display device to assist in interpreting the ultrasound image.

2. The ultrasound imaging system of claim 1, wherein the one or more pictographs represent a type of the first feature that is associated with the first view.

3. The ultrasound imaging system of claim 1, wherein the processor is configured to not display the one or more pictographs that do not represent the ultrasound image.

4. The ultrasound imaging system of claim 1, wherein each of the one or more pictographs is displayed with an indication of a likelihood to represent the ultrasound image.

5. The ultrasound imaging system of claim 1, wherein the one or more pictographs are displayed in an order that represents a likelihood for each pictograph to represent the ultrasound image.

6. The ultrasound imaging system of claim 1, wherein each of the one or more pictographs is displayed with a visual cue that indicates a likelihood that a pictograph corresponds to the ultrasound image.

7. The ultrasound imaging system of claim 6, wherein the visual cue is a color.

8. The ultrasound imaging system of claim 4, wherein the indication of the likelihood is a score.

9. The ultrasound imaging system of claim 1, wherein the processor is configured to provide pixel values of the ultrasound image as inputs to the trained neural network.

10. The ultrasound imaging system of claim 1, wherein the processor is configured to provide pre pixel image data for the ultrasound image as inputs to the trained neural network.

11. The ultrasound imaging system of claim 1, wherein the memory is configured to store the one or more pictographs.

12. The ultrasound imaging system of claim 1, wherein the neural network is configured to produce an indication of a likelihood for the ultrasound data to represent a tissue type and the processor is configured to display the one or more pictographs that most likely represent the tissue type of the ultrasound image.

13. The ultrasound imaging system of claim 1, wherein the neural network is configured to produce an indication of a likelihood that the ultrasound data are obtained using the first view and the processor is configured to display the one or more pictographs that most likely represent the first view.

14. The ultrasound imaging system of claim 1, wherein the neural network is configured to produce an indication of a likelihood that an area in the ultrasound image represents a tissue feature and the processor is configured to display the one or more pictographs in the area of the ultrasound image based on the indication from the neural network.

15. An ultrasound imaging system, comprising:
   a memory; and
   a processor coupled to the memory that is configured to:
      determine one or more first views for an ultrasound image to be included into a patient record for a particular examination type,
      wherein the processor is further configured to: provide ultrasound image data to one or more trained neural networks; receive, from the one or more neural networks, a first value indicating a probability that the ultrasound image is of a first feature based on the ultrasound image data; receive, from the one or more neural networks, a second value indicating the probability that the ultrasound image is of a first view based on the first value; determine one or more second views for the ultrasound image based on the second value, and to produce an indication of a likelihood of the one or more second views correspond to the one or more first views, wherein the one or more first views correspond to a desired view of the ultrasound image to be included into the patient record and the one or more second views corresponding to a viewing position of an imaging probe from which the ultrasound image is captured are determined using the one or more trained neural networks.

16. The ultrasound imaging system of claim 15, wherein the processor is configured to:
   identify data for one or more ultrasound images that correspond to a first view;
   present the one or more ultrasound images to an operator on the display device;
   determine if the operator has selected the one or more ultrasound images; and incorporate the one or more ultrasound images into the patient record.

17. The ultrasound imaging system of claim 15, wherein the processor is configured to incorporate the ultrasound image that corresponds to a first view into the patient report.

18. The ultrasound imaging system of claim 15, wherein the processor is configured to alert an user that the ultrasound image data correspond to a first view.

19. The ultrasound imaging system of claim 15, wherein the processor is configured to provide an indication to the user if images corresponding to the one or more first views have been identified.

20. An ultrasound imaging system, comprising:
   a memory; and
   a processor coupled to the memory that is configured to:
      provide data for an ultrasound image obtained using one or more first imaging parameters to one or more neural networks that are trained to classify the ultrasound image, wherein the one or more first imaging parameters were previously set on the ultrasound imaging system to obtain the ultrasound image;

receive, from the one or more neural networks, a first value indicating a probability that the ultrasound image is of first feature for;

compare one or more current imaging parameters that are set on the ultrasound imaging system against the one or more first imaging parameters;

determine that the one or more current imaging parameters set on the ultrasound imaging system correspond to the first feature based on the comparing;

if the one or more current imaging parameters set on the ultrasound imaging system correspond to the first feature, increase the first value; and if the one or more current imaging parameters set on the ultrasound imaging system do not correspond to the first feature, prompt an operator to check the one or more current imaging parameters to reduce a likelihood that an incorrect set of imaging parameters is used to perform an examination.

21. The ultrasound imaging system of claim 20, wherein the one or more neural networks is trained to classify the data for the ultrasound image as corresponding to the first feature.

* * * * *